(12) United States Patent
Han

(10) Patent No.: US 12,576,269 B2
(45) Date of Patent: Mar. 17, 2026

(54) ELECTRONIC DEVICE USING LOW FREQUENCY AND METHOD OF OPERATION THEREOF

(71) Applicant: ION INTERNATIONAL CO.LTD, Hanam-si (KR)

(72) Inventor: Jungwoo Han, Namyangju-si (KR)

(73) Assignee: ION INTERNATIONAL CO.LTD, Hanam-si (KR)

( * ) Notice: Subject to any disclaimer, the term of this patent is extended or adjusted under 35 U.S.C. 154(b) by 621 days.

(21) Appl. No.: 18/078,007

(22) Filed: Dec. 8, 2022

(65) Prior Publication Data

US 2023/0109100 A1     Apr. 6, 2023

Related U.S. Application Data

(63) Continuation of application No. PCT/KR2021/009547, filed on Jul. 23, 2021.

(30) Foreign Application Priority Data

Aug. 7, 2020     (KR) ......................... 10-2020-0098912

(51) Int. Cl.
    *A61N 1/36*     (2006.01)
    *A61B 90/00*     (2016.01)
    (Continued)

(52) U.S. Cl.
    CPC .............. *A61N 1/321* (2013.01); *A61F 7/007* (2013.01); *A61N 1/36003* (2013.01)

(58) Field of Classification Search
    CPC .. A61N 1/321; A61N 1/36003; A61N 1/3603; A61N 1/36042; A61N 1/048;
    (Continued)

(56) References Cited

U.S. PATENT DOCUMENTS

2002/0058972 A1*  5/2002  Minogue ................ A61N 1/321
                         607/72
2005/0043655 A1*  2/2005  Schenck ................ A61N 1/321
                         601/71
(Continued)

FOREIGN PATENT DOCUMENTS

EP         1911490 A1 *  4/2008  ......... A61N 1/36007
JP       H11309219 A    11/1999
          (Continued)

OTHER PUBLICATIONS

International search report of PCT/KR2021/009547, Nov. 1, 2021, English translation.

*Primary Examiner* — Carl H Layno
*Assistant Examiner* — Anh-Khoa N Dinh
(74) *Attorney, Agent, or Firm* — STIP Law Group LLC

(57) ABSTRACT

An electronic device using a low frequency includes a belt, detachable electrode pads, and a control box that generates and controls stimulation signals. A cable within the belt includes a first line and a second line branching obliquely from a mid-portion of the first line at an angle of 30°-90°, forming a T-shaped configuration to supply independent frequency signals to the respective pads. Each pad is independently detachable from the belt for cleaning or replacement and includes Velcro disposed on both surfaces for reversible attachment. One surface of each pad may include a woven silver-plated conductive layer, and the opposite surface may include a carbon-based resistive heating film to provide combined electrical and thermal stimulation. The control box stores and executes instructions to automatically transition between multiple frequency signals according to predefined time intervals, thereby providing adaptive low-frequency stimulation for improved comfort and usability.

20 Claims, 11 Drawing Sheets

(51) Int. Cl.
  *A61F 7/00*        (2006.01)
  *A61N 1/32*        (2006.01)
(58) Field of Classification Search
  CPC .. A61N 1/0492; A61N 1/0452; A61N 1/0476;
        A61N 1/36034; A61N 1/0456; A61N
        1/0484; A61N 1/36014; A61N 1/36021;
        A61N 1/0468; A61N 1/20; A61N 1/32;
        A61N 1/328; A61N 2/06; A61N
        2005/06437; A61F 7/007; A61B 2090/065
  See application file for complete search history.

(56)              References Cited

U.S. PATENT DOCUMENTS

2006/0270952  A1*  11/2006  Freeman ............. A61H 31/005
                                              601/41
2009/0171418  A1*   7/2009  Sarif ...................... A61N 1/321
                                              607/2

2013/0085553  A1*   4/2013  Kang ........................ A61F 7/08
                                              607/100
2015/0020287  A1*   1/2015  Liu ......................... A41B 9/001
                                              2/69
2016/0235981  A1*   8/2016  Southwell ......... A61N 1/36007

FOREIGN PATENT DOCUMENTS

| | | | |
|---|---|---|---|
| JP | 2008173487 | A | 7/2008 |
| JP | 2016163663 | A | 9/2016 |
| JP | 2018102756 | A | 7/2018 |
| KR | 2020110007113 | U | 7/2011 |
| KR | 101093103 | B1 | 12/2011 |
| KR | 20180125164 | A | 11/2018 |
| KR | 20190010154 | A | 1/2019 |
| KR | 102214255 | B1 | 2/2021 |
| WO | WO2015122014 | A1 | 8/2015 |

* cited by examiner

ELECTRONIC DEVICE USING LOW FREQUENCY AND METHOD OF OPERATION THEREOF

CROSS-REFERENCE TO RELATED APPLICATIONS

This application is a continuation of Application No. PCT/KR2021/009547, filed on Jul. 23, 2021, which in turn claims the benefit of Korean Patent Application No. 10-2020-0098912, filed on Aug. 7, 2020, the disclosures of which are incorporated by reference into the present application.

TECHNICAL FIELD

The present invention relates to an electronic device using a low frequency and a method of operating the electronic device.

BACKGROUND ART

An electronic device using a low frequency may cause contraction and relaxation of muscles in the user's body part by applying low-frequency stimulation to the user's body part using a belt that wraps the user's body part.

On the other hand, the electronic device using a low frequency may be manufactured integrally with accessories included in the electronic device using a low frequency. When the accessories included in the electronic device using a low frequency are manufactured integrally with the electronic device, it may be difficult to determine which part needs to be repaired when the electronic device needs to be repaired.

In addition, the electronic device using a low frequency may provide a certain frequency signal to a user in a mode selected by the user. Accordingly, in order to receive various frequency signals, it may be inconvenient to constantly change the mode.

DESCRIPTION OF EMBODIMENTS

Technical Problem

A user may use an electronic device using a low frequency in parallel with exercise. When accessories included in the electronic device using a low frequency are manufactured integrally with the electronic device, it may not be easy to remove contaminants. In addition, when accessories included in the electronic device using a low frequency are manufactured integrally with the electronic device, when a defect occurs in the electronic device, the entire electronic device may have to be replaced. Furthermore, when a defect occurs in the electronic device, the entire electronic device may have to be replaced. In addition, when only a certain frequency signal is provided in at least one mode that can be provided by the electronic device using a low frequency, if a user wants stimulation by another frequency signal, there may be an inconvenience of additionally changing the mode.

According to an embodiment disclosed in this document, because accessories included in the electronic device using a low frequency are detachable, contaminants may be easily removed, and when a defect occurs, only a defective accessory may be replaced, thereby providing convenience to a user. In addition, the electronic device using a low frequency may provide convenience to a user by providing various frequency signals in a specific mode.

Technical Solution

An electronic device using a low frequency according to an embodiment of the present disclosure may include: a belt; a cable including a first line extending in a first direction and a second line extending from between one end and the other end of the first line in a second direction crossing the first direction; a first pad detachably attached to a rear surface of the belt and connected to the one end of the first line on the rear surface of the belt; a second pad detachably attached to the rear surface of the belt and connected to the second line on the rear surface of the belt; and a control box detachably attached to the belt and including a processor, wherein the other end of the first line passes through the belt and is connected to the control box on the front surface of the belt, and a position to which the first pad is attached on the rear surface of the belt and a position to which the second pad is attached on the rear surface of the belt are adjustable.

An electronic device using a low frequency according to another embodiment of the present disclosure may include: a belt; a first pad and a second pad that are detachably attached to a rear surface of the belt, wherein a position to which the first pad is attached on the rear surface of the belt and a position to which the second pad is attached on the rear surface of the belt are adjustable; a control box detachably attached to the belt and including a processor; and a memory operatively coupled to the processor, the memory storing instructions; and the processor configured to execute the instructions to: provide a first mode that lasts for a first time and a second mode that lasts for a second time; sequentially provide a plurality of frequency signals having different frequencies during the first time in the first mode; and provide a first frequency signal that is any one of the plurality of frequency signals during the second time in the second mode.

Advantageous Effects of Disclosure

According to embodiments disclosed in this document, user convenience may be increased and efficient management of an electronic device using a low frequency may be possible.

In addition, various effects directly or indirectly identified through this document may be provided.

BRIEF DESCRIPTION OF DRAWINGS

In the description of the drawings, the same or similar reference numerals may be used for the same or similar components.

MODE OF DISCLOSURE

Hereinafter, various embodiments of the present invention will be described with reference to the accompanying drawings. However, this is not intended to limit the present invention to specific embodiments, and it should be understood that various modifications, equivalents, and/or alternatives of the embodiments of the present invention are included.

Figure 1:
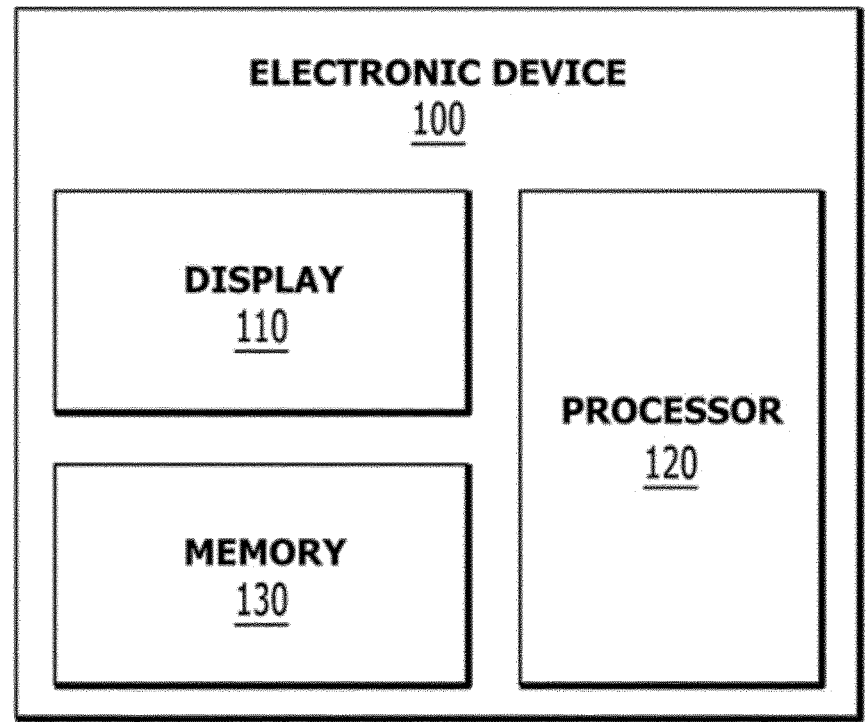
FIG. 1 is a block diagram of an electronic device 100 using a low frequency according to an embodiment disclosed in this document.

FIG. 1 is a block diagram of an electronic device 100 using a low frequency according to an embodiment disclosed in this document.

According to an embodiment, the electronic device 100 using a low frequency may include a display 110, a processor 120, or a memory 130. In some embodiments, in the electronic device 100, at least one (e.g., display 110) of these components may be omitted or one or more other components may be added.

The electronic device 100 using a low frequency may be, for example, an electronic device that provides a frequency signal of 20 Hz to 80 Hz.

The display 110 may visually provide information to the outside (e.g., a user) of the electronic device 100 using a low frequency. According to an embodiment, the display 110 may include a touch circuitry configured to sense a touch, or a sensor circuitry (e.g., a pressure sensor) configured to measure the intensity of a force generated by the touch.

The display 110 may display a mode of the electronic device 100 using a low frequency. For example, the display 110 may display a screen corresponding to a selected mode based on a mode selection signal received from a user.

For example, the processor 120 may execute software to control at least one other component (e.g., at least one pad) of the electronic device 100 using a low frequency connected to the processor 120. The processor 120 may be operatively coupled to the display 110 and the memory 130 to perform all functions of the electronic device 100 using a low frequency.

The processor 120 may provide a frequency signal based on the mode selection signal. Details on this will be described later with reference to FIGS. 11 to 14.

The memory 130 may store various data used by at least one component of the electronic device 100 using a low frequency. The data may include, for example, input data or output data for software and instructions related thereto.

Hereinafter, the electronic device 100 using a low frequency according to an embodiment disclosed in this document will be described with reference to FIGS. 2 to 10. Hereinafter, for clarity of description, descriptions overlapping those described above will be simplified or omitted.

Figure 2:
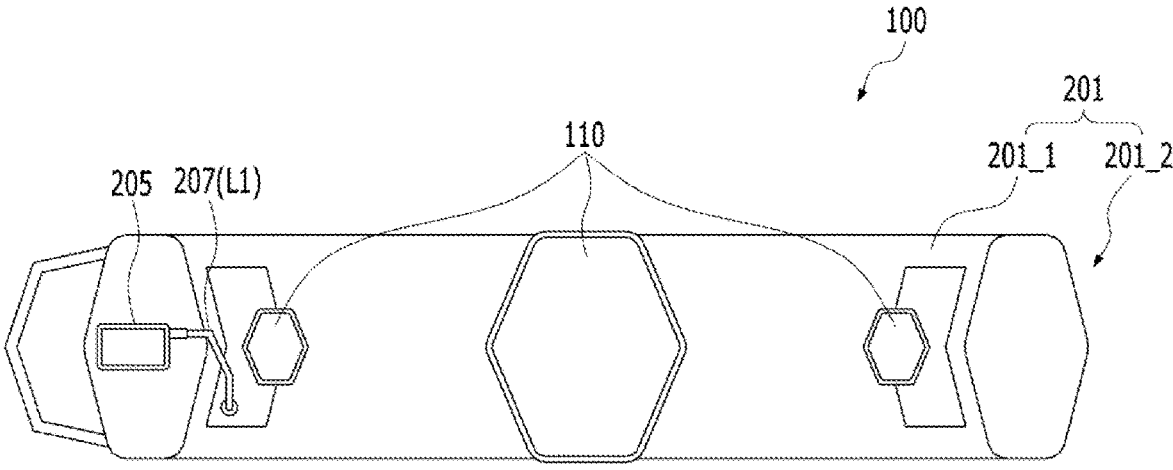
FIG. 2 is a view for explaining a front surface 201_1 of a belt 201 of the electronic device 100 using a low frequency according to an embodiment disclosed in this document.
Figure 3:
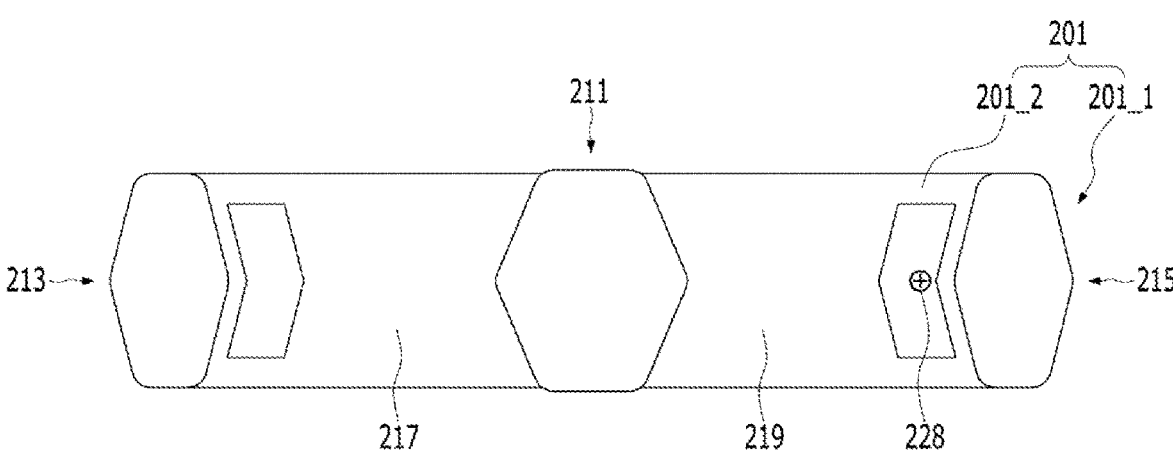
FIG. 3 is a view for explaining a rear surface 201_2 of the belt 201 of the electronic device 100 using a low frequency.
Figure 4:
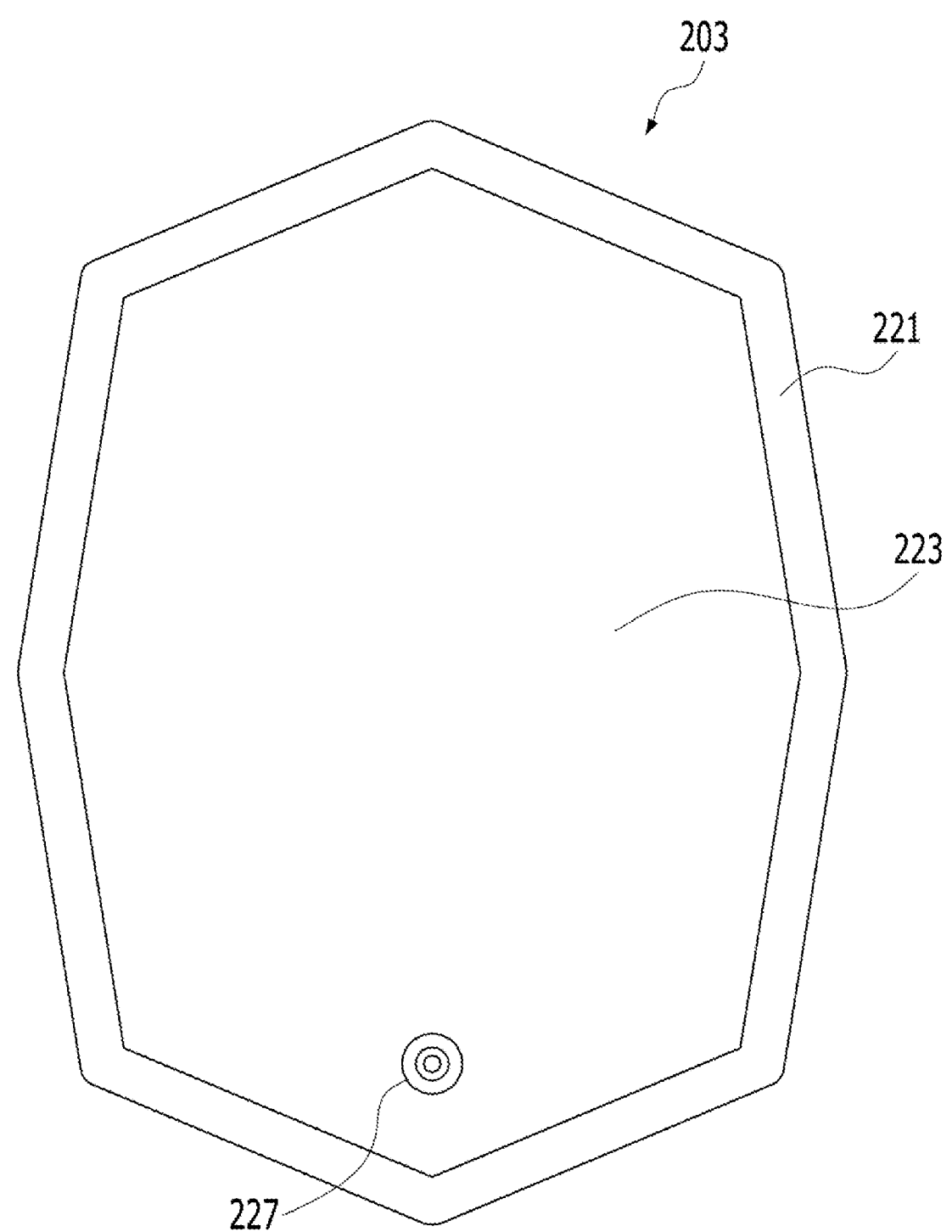
FIG. 4 is a view for explaining at least one pad 203 of the electronic device 100 using a low frequency according to an embodiment disclosed in this document.
Figure 5:
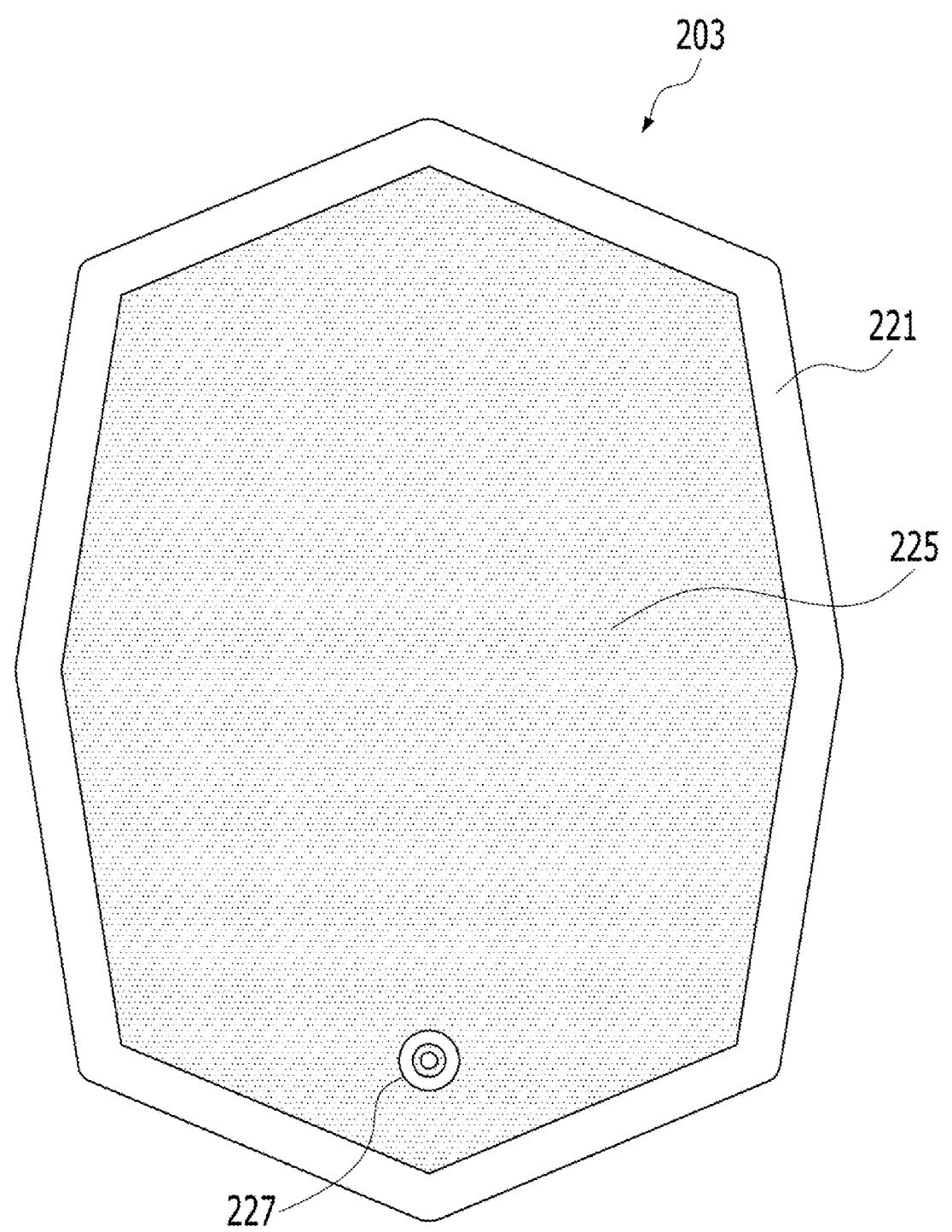
FIG. 5 is a view for explaining at least one pad 203 of the electronic device 100 using a low frequency according to an embodiment disclosed in this document.

FIG. 2 is a view for explaining a front surface 201_1 of a belt 201 of the electronic device 100 using a low frequency according to an embodiment disclosed in this document. FIG. 3 is a view for explaining a rear surface 201_2 of the belt 201 of the electronic device 100 using a low frequency. FIG. 4 is a view for explaining at least one pad 203 of the electronic device 100 using a low frequency according to an embodiment disclosed in this document. FIG. 5 is a view for explaining at least one pad 203 of the electronic device 100 using a low frequency according to an embodiment disclosed in this document.

Referring to FIGS. 2 to 5, the electronic device 100 using a low frequency may include the display 110, at least one pad 203, the belt 201, a control box 205, and the cable 207.

The display 110 may be disposed on the front surface 201_1 of the belt 201. Although FIG. 2 illustrates that three displays 110 are on the front surface 201_1 of the belt 201, the present invention is not limited thereto. For example, the number of displays 110 on the belt 201 may be changed as needed.

The control box 205 may be connected to the belt 201 and/or the pad 203 by the cable 207 on the front surface 201_1 of the belt 201. The control box 205 may be detachably attached to the belt 201 and/or the pad 203 by the cable 207. In other words, the control box 205 may be separated from or connected to the belt 201 and/or the pad 203.

The control box 205 may include a processor (e.g., the processor 120 in FIG. 1) and/or a memory (e.g., the memory 130 in FIG. 1) for operating the electronic device 100 using a low frequency. The control box 205 may include, for example, a receiving circuit capable of receiving a user's input. In an embodiment, the control box 205 may further include the display 110.

Although FIG. 2 illustrates that the control box 205 is attached to a specific position of the belt 201, the present invention is not limited thereto. For example, the control box 205 may be attached to any position of the belt 201 as needed.

The rear surface 201_2 of the belt 201 may include a point 211 bisecting the belt 201, a first surface 217 between one end 213 of the belt 201 and a point 211, and a second surface 219 between the other end 215 of the belt 201 and the point 211.

A penetrating portion 228 may be a portion penetrating the belt 201. Through the penetrating portion 228, the cable 207 may pass through the belt 201. In the drawings, the penetrating portion 228 is shown to be on the second surface 219, but is not limited thereto. The penetrating portion 228 may be in any position on the belt 201 as desired. In the drawings, the penetrating portion 228 is shown as one, but is not limited thereto. If necessary, a plurality of penetrating portions 228 may be arranged. In the drawings, the penetrating portion 228 is illustrated as having a specific shape, but is not limited thereto.

The at least one pad 203 may be detachably attached to the belt 201. In other words, the at least one pad 203 may be separated from or connected to the belt 201.

In an embodiment, the at least one pad 203 may be detachably attached to the rear surface 201_2 of the belt 201. For example, the at least one pad 203 may be on at least one of the first surface 217 and the second surface 219. Details on this will be described later.

The at least one pad 203 may include a first surface 223 and a second surface 225 facing each other. The first surface 223 and the second surface 225 of the at least one pad 203 may include Velcro 221 arranged along a circumference of the at least one pad 203. The at least one pad 203 may be attached to the belt 201 by the Velcro 221.

The at least one pad 203 is illustrated as having a specific shape in the drawing, but is not limited thereto. For example, the at least one pad 203 may have various shapes as needed.

The at least one pad 203 may include a connection portion 227. As the cable 207 and the connection part 227 are connected to each other, the at least one pad 203 may be connected to the control box 205.

In an embodiment, one surface of the at least one pad 203 may include a polyamide fiber and silver. For example, one surface of the at least one pad 203 may be a polyamide fiber plated with silver. For example, one surface of the at least one pad 203 may be woven with silver-plated threads. In this case, the at least one pad 203 may function as a conductor.

In an embodiment, the first surface 223 of the at least one pad 203 may include a conductive material, and the second surface 225 of the at least one pad 203 may include a heating material. For example, the first surface 223 of the at least one pad 203 may include silver. In other words, the first surface 223 of the at least one pad 203 may be woven with silver-plated threads.

Figure 6:
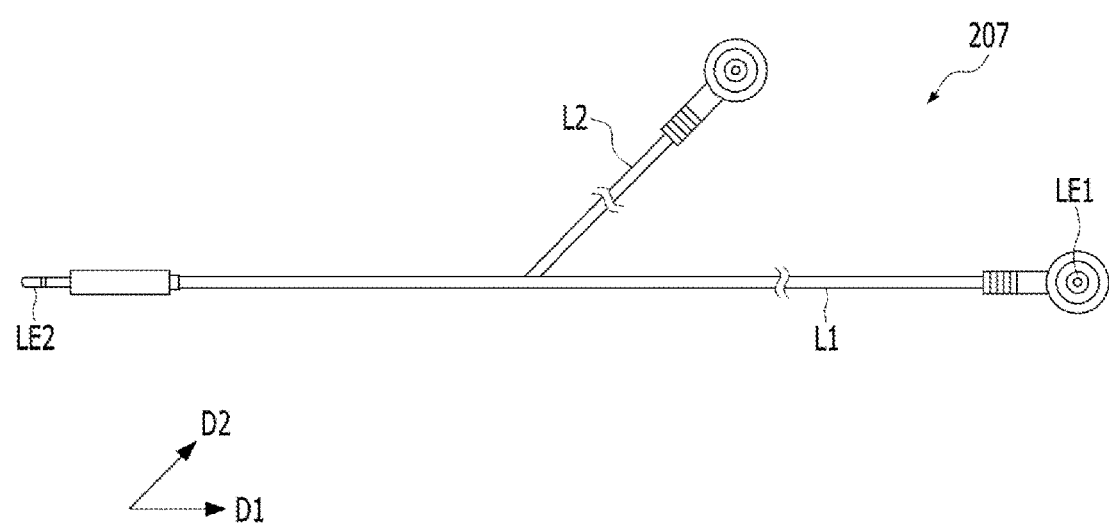
FIG. 6 is a view for explaining a cable 207 included in the electronic device 100 using a low frequency according to an embodiment disclosed in this document.

FIG. 6 is a view for explaining a cable 207 included in the electronic device 100 using a low frequency according to an embodiment disclosed in this document.

Referring to FIG. 6, the cable 207 may include a first line L1 and a second line L2. The first line L1 of the cable 207 may extend in a first direction D1. The second line L2 of the cable 207 may extend in a second direction D2 from between one end LE1 and the other end LE2 of the first line L1 of the cable 207. The first direction D1 may be a direction crossing the second direction D2.

At least one of the one end LE1 of the first line L1 and the second line L2 of the cable 207 may be connected to the at least one pad 203 through the connection portion 227 of the at least one pad 203 on the rear surface 201_2 of the belt 201. The other end LE2 of the first line L1 of the cable 207 may be connected to the control box 205 at the front surface 201_1 of the belt 201 through the belt 201 as shown in FIG. 2.

In an embodiment, one end LE1 of the cable 207 may be in the form of a button, and the other end LE2 of the cable 207 may be in the form of an earphone jack.

FIGS. 7 to 10 are views for explaining that at least one pad 203 is attached to the belt 201 from the rear surface 201_2 of the belt 201 according to an embodiment disclosed in this document.

In an embodiment, the at least one pad 203 may include a first pad 2031 and a second pad 2032. For example, the first pad 2031 may be on at least one of the first surface 217 and the second surface 219, and the second pad 2032 may be on at least one of the first surface 217 and the second surface 219.

The at least one pad 203 may be on the belt 201 such that the belt 201 comes into contact with either the first surface 217 or the second surface 219.

Figure 7:
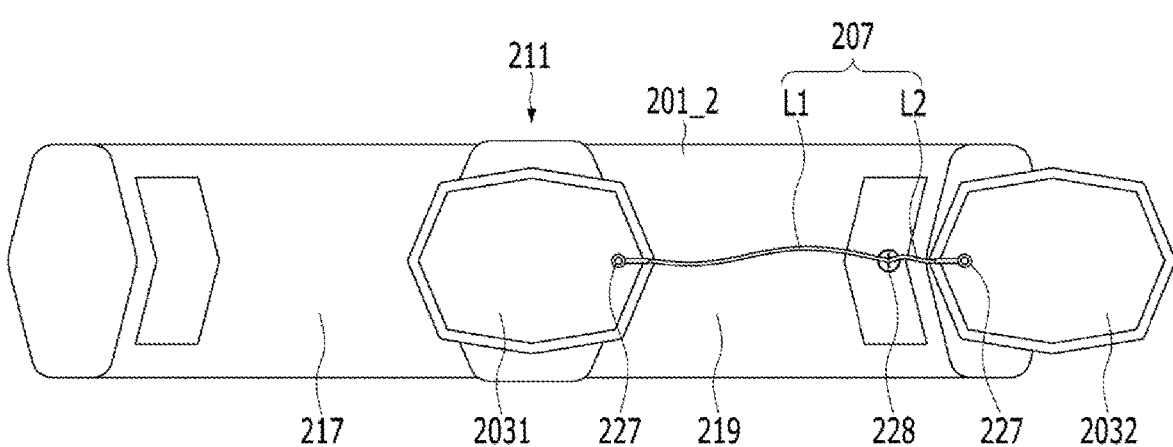
FIGS. 7 to 10 are views for explaining that at least one pad 203 is attached to the belt 201 from the rear surface 201_2 of the belt 201 according to an embodiment disclosed in this document.

Referring to FIG. 7, on the rear surface 201_2 of the belt 201, the first pad 2031 may be disposed over the first surface

217 and the second surface 219 of the belt 201. The second pad 2032 may be on the second surface 219 of the belt 201. In an embodiment of FIG. 7, only a portion of the second pad 2032 may be in contact with the second surface 219 of the belt 201. The one end LE1 of the first line L1 of the cable 207 may be coupled to the connection portion 227 of the first pad 2031. The second line L2 of the cable 207 may be coupled to the connection portion 227 of the second pad 2032. The first pad 2031 and the second pad 2032 may be connected to each other at the rear surface 201_2 of the belt 201 through the cable 207. As shown in FIG. 2, the other end LE2 of the first line L1 of the cable 207 may pass through the belt 201 through the penetrating portion 228 of the belt 201, and may be connected to the control box 205 on the front surface 201_1 of the belt 201.

Figure 8:
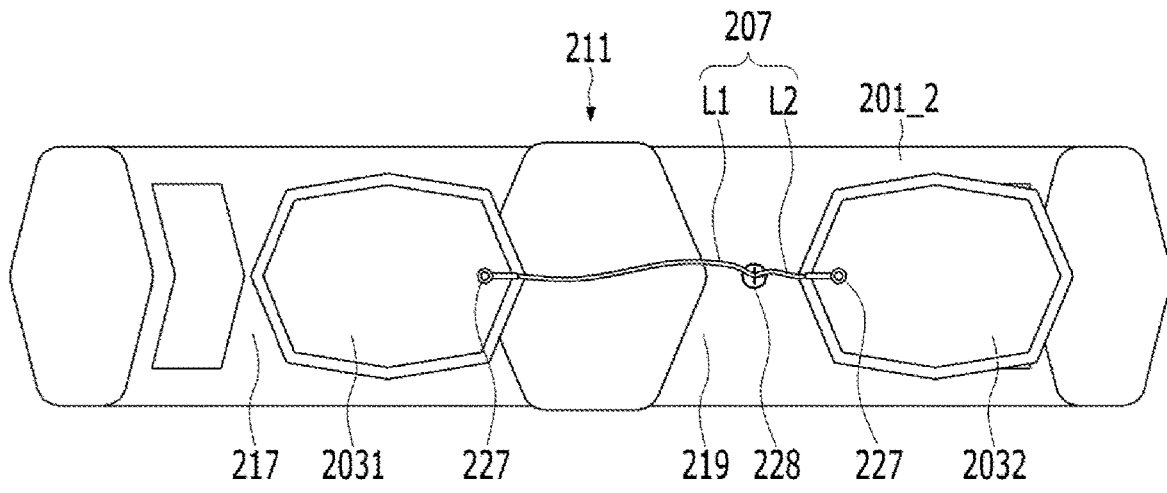

Referring to FIG. 8, on the rear surface 201_2 of the belt 201, the first pad 2031 may be on the first surface 217 of the belt 201, and the second pad 2032 may be on the second surface 219 of the belt 201.

Figure 9:
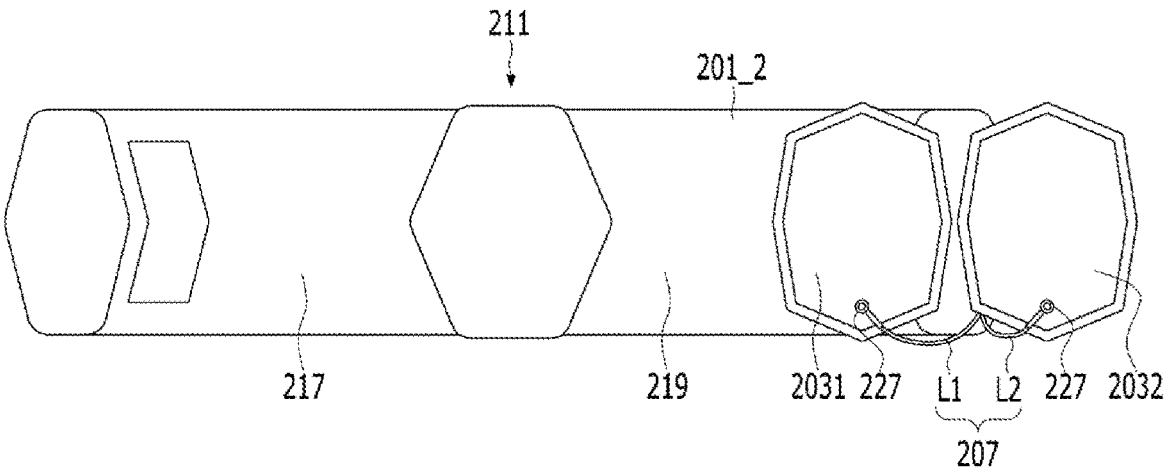

Referring to FIG. 9, on the rear surface 201_2 of the belt 201, the first pad 2031 and the second pad 2032 may be on the second surface 219 of the belt 201. However, the present invention is not limited thereto, and the first pad 2031 and the second pad 2032 may be on the first surface 217 of the belt 201.

Figure 10:
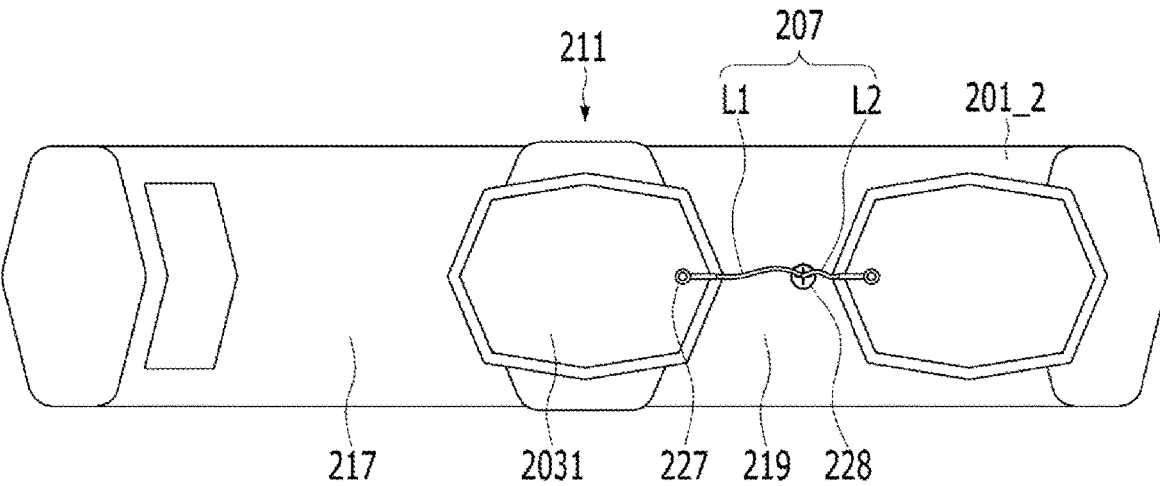

Referring to FIG. 10, on the rear surface 201_2 of the belt 201, the first pad 2031 may be disposed over the first surface 217 and the second surface 219 of the belt 201. The second pad 2032 may be on the second surface 219 of the belt 201. In an embodiment of FIG. 10, the second pad 2032 may be in contact with the second surface 219 of the belt 201. A user with a large size of the belt 201 may adjust the size by adjusting the position of the second pad 2032 and attaching the second pad 2032 to the belt 201.

The at least one pad 203 included in the electronic device 100 using a low frequency according to an embodiment disclosed in this document may be at an arbitrary position on the rear surface 201_2 of the belt 201 by being detachably attached to the belt 201 using the Velcro 221. By adjusting the position of the at least one pad 203 and attaching the at least one pad 203 to the belt 201, a user may adjust the size of the belt 201 so that the at least one pad 203 may be located at a desired position. In addition, by adjusting the position of the pad 203, general management (training) of the user's abdomen (front), lumbar region, flanks, etc. may be possible.

Hereinafter, an operation of the electronic device 100 using a low frequency according to an embodiment disclosed in this document will be described with reference to FIGS. 1, 11, 12, 13, and 14. Hereinafter, for clarity of description, descriptions overlapping those described above will be simplified or omitted.

Figure 11:
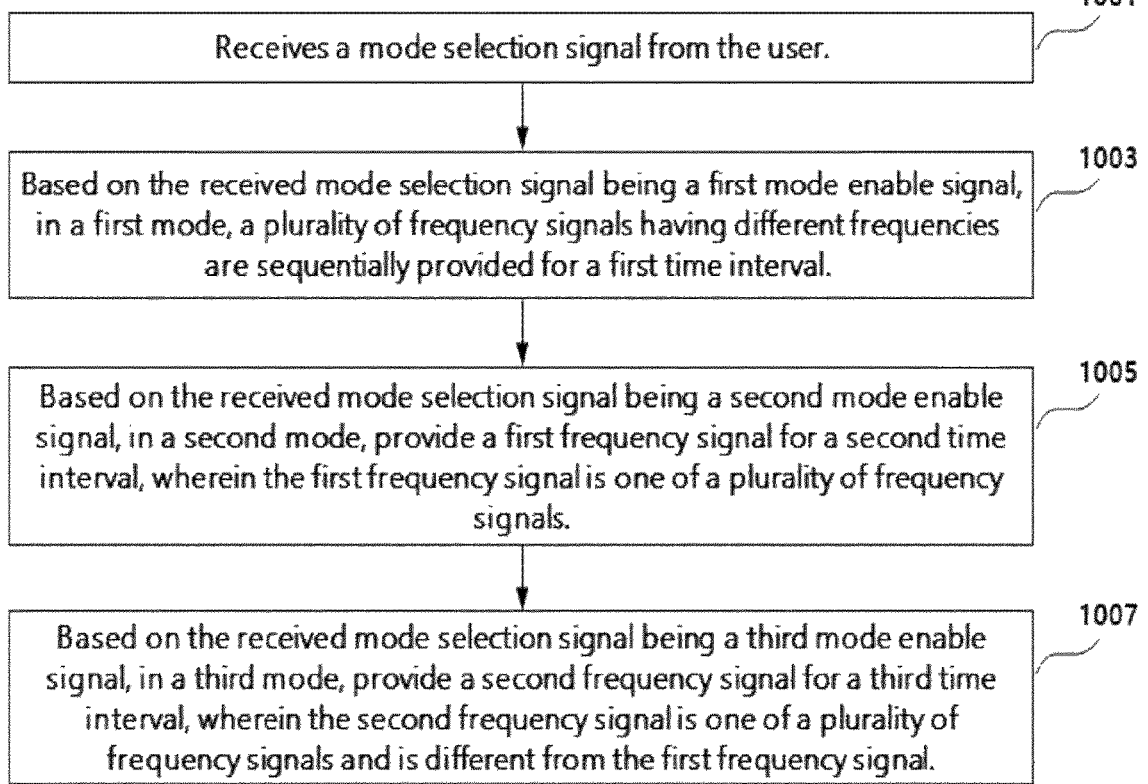
FIG. 11 is a view for explaining an operation of the electronic device 100 using a low frequency, according to an embodiment disclosed in this document.

FIG. 11 is a view for explaining an operation of the electronic device 100 using a low frequency, according to an embodiment disclosed in this document.

Hereinafter, it is assumed that the electronic device 100 using a low frequency of FIG. 1 performs a process of FIG. 11. An operation described as being performed by the electronic device 100 using a low frequency may be implemented as instructions (commands) that may be performed (or, executed) by the processor 120. The instructions may be stored in, for example, a computer recording medium or the memory 130.

Figure 12:
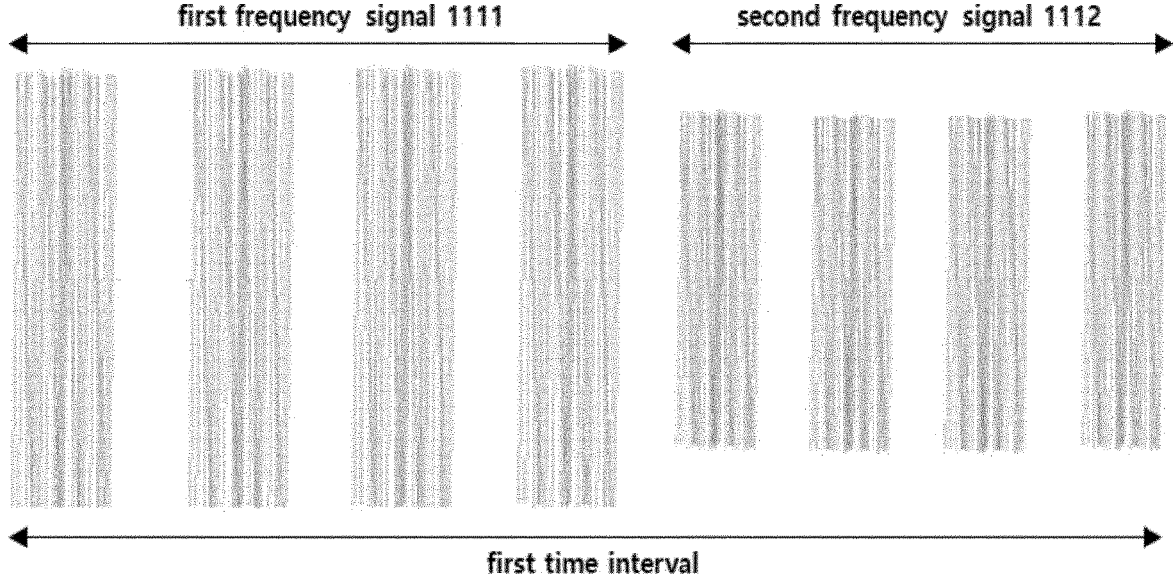
FIG. 12 is a view for explaining a first mode provided by the electronic device 100 using a low frequency according to an embodiment disclosed in this document.
Figure 13:
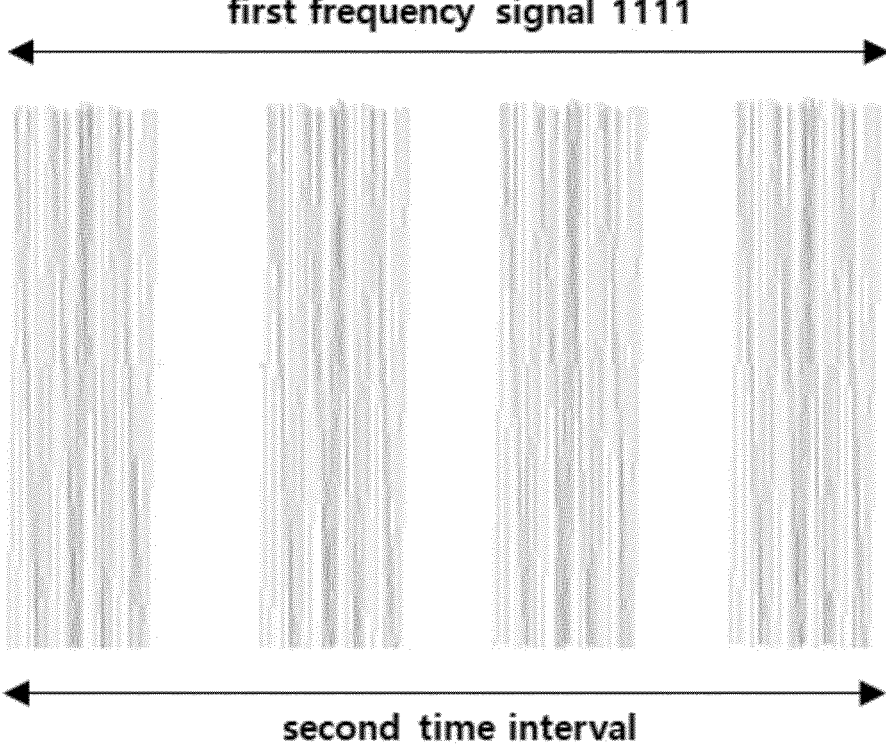
FIG. 13 is a view for explaining a second mode provided by the electronic device 100 using a low frequency according to an embodiment disclosed in this document.
Figure 14:
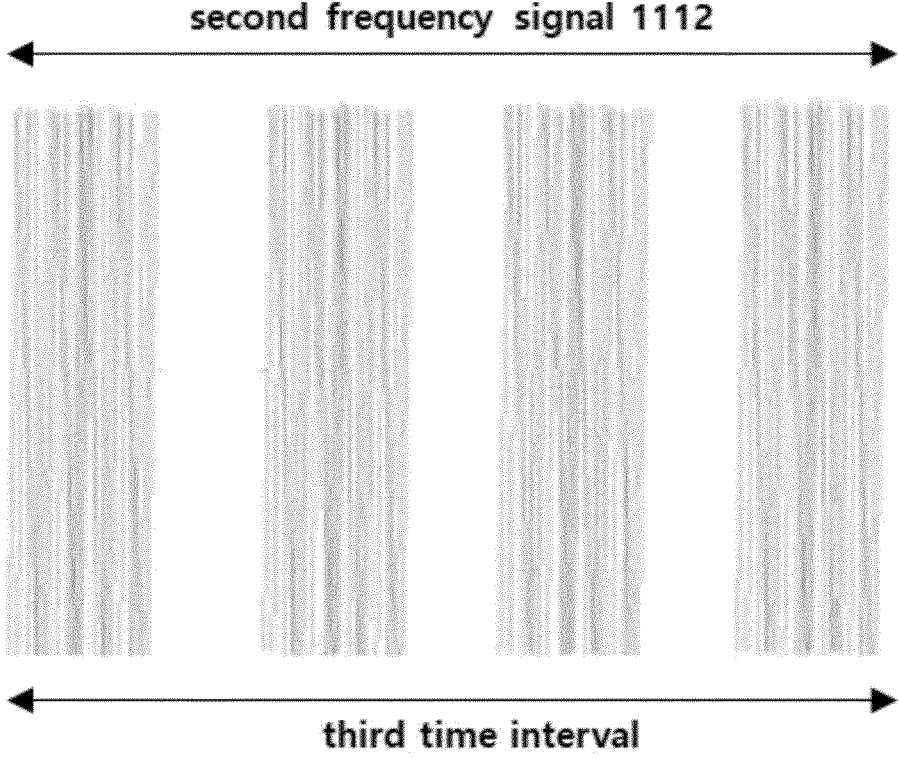
FIG. 14 is a view for explaining a third mode provided by the electronic device 100 using a low frequency according to an embodiment disclosed in this document.

FIG. 12 is a view for explaining a first mode provided by the electronic device 100 using a low frequency according to an embodiment disclosed in this document. FIG. 13 is a view for explaining a second mode provided by the electronic device 100 using a low frequency according to an embodiment disclosed in this document. FIG. 14 is a view for explaining a third mode provided by the electronic device 100 using a low frequency according to an embodiment disclosed in this document.

Referring to FIG. 11, in operation 1001, the electronic device 100 using a low frequency may receive a mode selection signal from a user. For example, the electronic device 100 using a low frequency may provide one or more modes. The user may select one of modes provided by the electronic device 100 using a low frequency.

In operation 1003, the electronic device 100 using a low frequency may sequentially provide a plurality of frequency signals having different frequencies during a first time in a first mode based on that the received mode selection signal is a first mode execution signal. For example, as illustrated, the electronic device 100 using a low frequency may sequentially provide a first frequency signal and a second frequency signal. For convenience of explanation, it is described that the first and second frequency signals are provided in the first mode, but this is exemplary, and three different frequency signals or more frequency signals may be provided. The first mode execution signal may be a signal for executing the first mode selected by the user. Referring to FIG. 12, the first mode may last for the first time. The electronic device 100 using a low frequency may sequentially provide a first frequency signal 1111 and a second frequency signal 1112 during the first time in the first mode. For example, after providing the first frequency signal 1111 for a certain time, the electronic device 100 using low a frequency may provide the second frequency signal 1112 for at least a part of the remaining time of the first time. The second frequency signal 1112 may have a frequency different from that of the first frequency signal 1111. Although it has been described in FIG. 12 that two signals having different frequencies are provided during the first time in the first mode, the present invention is not limited thereto. For example, the electronic device 100 using a low frequency may further provide a third frequency signal having a frequency different from the frequency of the first frequency signal 1111 and the frequency of the second frequency signal 1112 during the remaining time after providing the first frequency signal 1111 and the second frequency signal 1112 during the first time in the first mode.

Referring back to FIG. 11, in operation 1005, the electronic device 100 using a low frequency may provide the first frequency signal that is any one of a plurality of frequency signals during a second time in a second mode based on that the received mode selection signal is a second mode execution signal. For example, an operation in the first mode and an operation in the second mode of the electronic device 100 using a low frequency may be different from each other. The second mode execution signal may be a signal for executing the second mode selected by the user. Referring to FIG. 13, the second mode may last for the second time. The electronic device 100 using a low frequency may not provide a signal having a frequency different from that of the first frequency signal 1111 during the second time in the second mode. For example, the second time may be the same as or different from the first time.

Referring back to FIG. 11, in operation 1007, the electronic device 100 using a low frequency may provide the second frequency signal different from the first frequency signal from among the plurality of frequency signals during a third time in a third mode based on that the received mode selection signal is a third mode execution signal. For example, the operation in the first mode, the operation in the second mode, and an operation in the third mode of the electronic device 100 using a low frequency may be different from each other. The third mode execution signal may be a signal for executing the third mode selected by the user. Referring to FIG. 14, the third mode may last for the third time. The electronic device 100 using low frequency may not provide a signal having a different frequency from that of the second frequency signal 1112 during the third time in the third mode. The first time, the second time, and the third time may be the same as or different from each other.

Hereinafter, the electronic device 100 using a low frequency according to an embodiment disclosed in this document will be described with reference to FIG. 15. Hereinafter, for clarity of description, descriptions overlapping those described above will be simplified or omitted.

Figure 15:
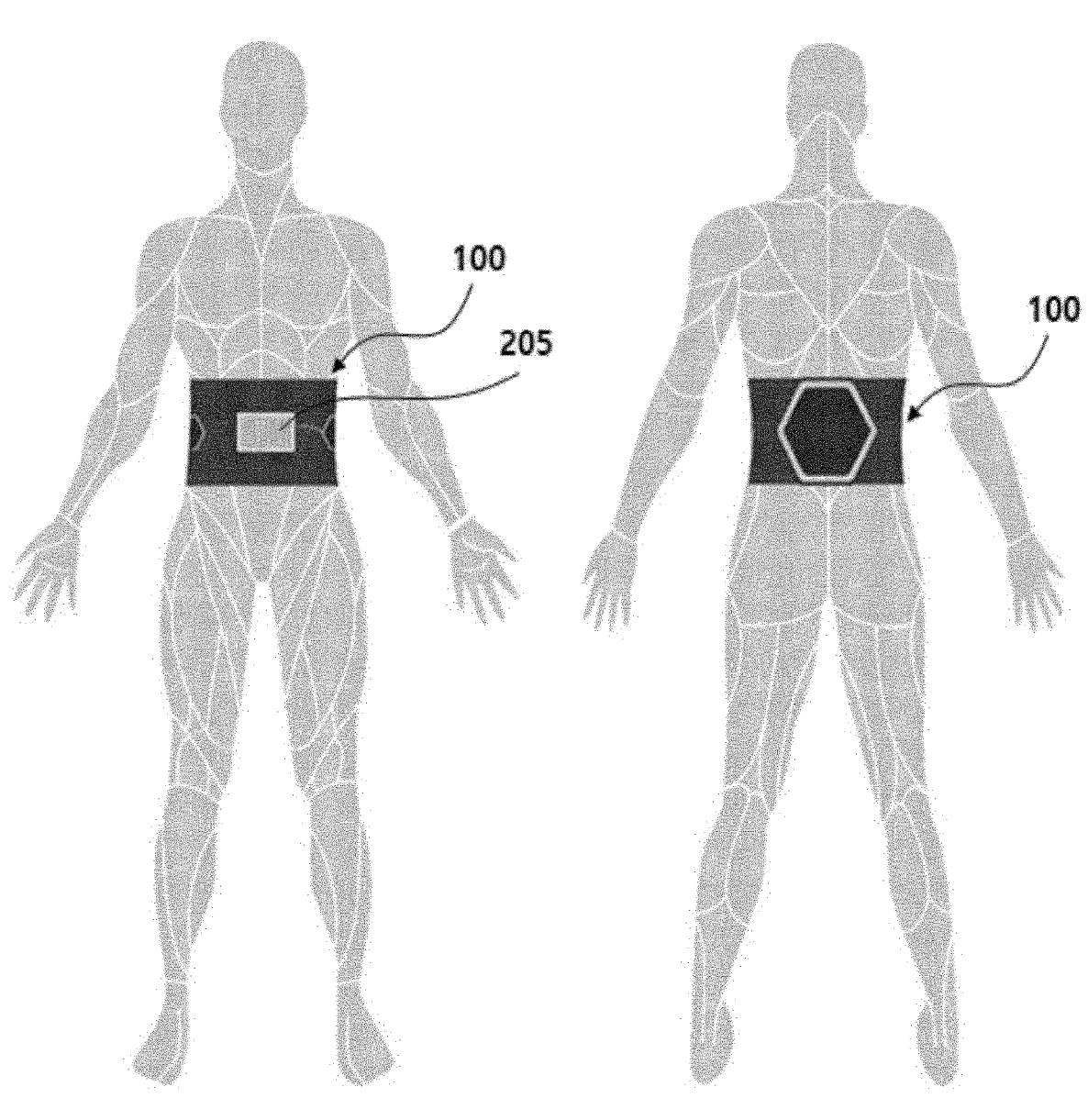
FIG. 15 is a view for explaining that the electronic device 100 using a low frequency according to an embodiment disclosed in this document is used.

FIG. 15 is a view for explaining that the electronic device 100 using a low frequency according to an embodiment disclosed in this document is used.

Referring to FIG. 15, in the electronic device 100 using a low frequency, the belt 201 of the electronic device 100 using a low frequency may be arranged to surround the user's abdomen and waist, and may be used to provide a signal having a certain frequency to the user's abdomen and/or waist through the at least one pad 203.

Although the present invention has been described in detail through representative embodiments above, one of ordinary skill in the art will understand that various modifications are possible without departing from the scope of the present invention in relation to the above-described embodiments. Therefore, the scope of the present invention should not be limited to the described embodiments, and should be defined by all changes or modifications derived from the claims and equivalent concepts as well as the claims to be described later.

The invention claimed is:

1. An electronic device using a low frequency comprising:
a belt;
a cable including a first line extending in a first direction and a second line extending from between one end and the other end of the first line in a second direction crossing the first direction;
a first pad detachably attached to a rear surface of the belt and connected to the one end of the first line on the rear surface of the belt;
a second pad detachably attached to the rear surface of the belt and connected to the second line on the rear surface of the belt; and
a control box detachably attached to the belt and including a processor,
wherein the second line branches obliquely from a midportion of the first line at an angle of 30° to 90°, forming a T-shaped cable configuration that allows the first and second pads to receive independent frequency signals,
wherein each of the first pad and the second pad is individually detachable from the belt for cleaning or replacement, and
wherein the other end of the first line passes through the belt and is connected to the control box on the front surface of the belt, and a position to which the first pad is attached on the rear surface of the belt and a position to which the second pad is attached on the rear surface of the belt are adjustable.

2. The electronic device using a low frequency of claim 1, further comprising:
a memory operatively coupled to the processor,
the memory storing instructions; and
the processor configured to execute the instructions to:
provide a first mode that lasts for a first time and a second mode that lasts for a second time;
automatically transition between a plurality of frequency signals having different frequencies during the first time in the first mode according to predefined intervals stored in the memory without user intervention; and
provide a first frequency signal that is any one of the plurality of frequency signals during the second time in the second mode.
3. The electronic device using a low frequency of claim 2, wherein the processor is further configured to execute the instructions not to provide a signal having a frequency different from that of the first frequency signal during the second time in the second mode, and
wherein the processor automatically maintains the first frequency signal according to a stored predefined interval without user intervention.
4. The electronic device using a low frequency of claim 2, wherein the processor is further configured to execute the instructions to:
provide a third mode that lasts for a third time;
provide a second frequency signal different from the first frequency signal from among the plurality of frequency signals during the third time in the third mode, and
the transition between the first and second frequency signals being automatically performed according to the predefined time intervals stored in the memory.
5. The electronic device using a low frequency of claim 4, wherein the processor is further configured to execute the instructions not to provide a signal having a frequency different from that of the second frequency signal during the third time in the third mode, and
to maintain the second frequency signal automatically for the duration of the third time.
6. The electronic device using a low frequency of claim 2, wherein the plurality of frequency signals comprises the first frequency signal and a second frequency signal different from the first frequency signal, and
the processor is further configured to execute the instructions to:
provide the first frequency signal at a predefined interval in a section in which the first frequency signal is provided during the first time in the first mode; and
provide the second frequency signal at a predefined interval in a section in which the second frequency signal is provided during the first time,
wherein the processor automatically alternates between the first and second frequency signals according to the predefined intervals stored in the memory, thereby providing continuous adaptive stimulation.
7. The electronic device using a low frequency of claim 1, wherein the first pad and the second pad comprise a flexible woven polyamide fiber plated with silver to provide a corrosion-resistant conductive layer.
8. The electronic device using a low frequency of claim 7, wherein each of the first pad and the second pad comprises a first surface and a second surface facing each other,
wherein the first surface comprises the woven silver-plated conductive layer of claim 7, and the second surface comprises a carbon-based resistive heating film thermally insulated from the conductive layer.

9. The electronic device using a low frequency of claim 1, wherein each of the first pad and the second pad comprises Velcro arranged along a circumference of each of the first pad and the second pad,
the Velcro being disposed on both surfaces of each pad so that either surface can be selectively attached to the rear surface of the belt according to a user's need, thereby improving convenience of use and hygiene management, and
each of the first pad and the second pad is attached to the rear surface of the belt using the Velcro.
10. The electronic device using a low frequency of claim 1, wherein the rear surface of the belt comprises a point bisecting the rear surface of the belt, a first surface between one end of the rear surface of the belt and the point, and a second surface between the other end of the rear surface of the belt and the point,
wherein the first pad overlaps the central point of the belt to contact a lumbar region, and the second pad overlaps the lateral surface of the belt to contact an oblique abdominal region, thereby enabling simultaneous stimulation of lumbar and abdominal muscles.
11. An electronic device using a low frequency comprising:
a belt;
a first pad and a second pad that are detachably attached to a rear surface of the belt, wherein a position to which the first pad is attached on the rear surface of the belt and a position to which the second pad is attached on the rear surface of the belt are adjustable;
a control box detachably attached to the belt and including a processor; and
a memory operatively coupled to the processor,
the memory storing instructions; and
the processor configured to execute the instructions to:
provide a first mode that lasts for a first time and a second mode that lasts for a second time;
automatically transition between a plurality of frequency signals having different frequencies during the first time in the first mode according to predefined intervals stored in the memory without user intervention; and
provide a first frequency signal that is any one of the plurality of frequency signals during the second time in the second mode.
12. The electronic device using a low frequency of claim 11, wherein the processor is further configured to execute the instructions not to provide a signal having a frequency different from that of the first frequency signal during the second time in the second mode, and
wherein the processor automatically maintains the first frequency signal according to a stored predefined interval without user intervention.
13. The electronic device using a low frequency of claim 11, wherein the processor is further configured to execute the instructions to:
provide a third mode that lasts for a third time; and
provide a second frequency signal different from the first frequency signal from among the plurality of frequency signals during the third time in the third mode,
the transition between the first and second frequency signals being automatically performed according to the predefined time intervals stored in the memory.

14. The electronic device using a low frequency of claim 13,
    wherein the processor is further configured to execute the instructions not to provide a signal having a frequency different from that of the second frequency signal during the third time in the third mode, and
    to maintain the second frequency signal automatically for the duration of the third time.

15. The electronic device using a low frequency of claim 11,
    wherein the plurality of frequency signals comprises the first frequency signal and a second frequency signal different from the first frequency signal, and
    the processor is further configured to execute the instructions to:
    provide the first frequency signal at a predefined interval in a section in which the first frequency signal is provided during the first time in the first mode; and
    provide the second frequency signal at a predefined interval in a section in which the second frequency signal is provided during the first time,
    wherein the processor automatically alternates between the first and second frequency signals according to the predefined intervals stored in the memory, thereby providing continuous adaptive stimulation.

16. The electronic device using a low frequency of claim 11, further comprising:
    a cable including a first line extending in a first direction and a second line extending from between one end and the other end of the first line in a second direction crossing the first direction,
    wherein the second line branches obliquely from a mid-portion of the first line at an angle of 30° to 90°, forming a T-shaped cable configuration that allows the first and second pads to receive independent frequency signals,
    wherein each of the first pad and the second pad is individually detachable from the belt for cleaning or replacement,
    and wherein one end of the first line is connected to the first pad on the rear surface of the belt, the second line is connected to the second pad on the rear surface of the belt, and the other end of the first line is connected to the control box through the belt on a front surface of the belt.

17. The electronic device using a low frequency of claim 11,
    wherein the first pad and the second pad comprise a flexible woven polyamide fiber plated with silver to provide a corrosion-resistant conductive layer.

18. The electronic device using a low frequency of claim 17,
    wherein each of the first pad and the second pad comprises a first surface and a second surface facing each other,
    wherein the first surface comprises the woven silver-plated conductive layer of claim 17, and the second surface comprises a carbon-based resistive heating film thermally insulated from the conductive layer.

19. The electronic device using a low frequency of claim 11,
    wherein each of the first pad and the second pad comprises Velcro arranged along a circumference of each of the first pad and the second pad,
    the Velcro being disposed on both surfaces of each pad so that either surface can be selectively attached to the rear surface of the belt according to a user's need, thereby improving convenience of use and hygiene management, and
    each of the first pad and the second pad is attached to the belt using the Velcro.

20. The electronic device using a low frequency of claim 11,
    wherein the rear surface of the belt comprises a point bisecting the rear surface of the belt, a first surface between one end of the rear surface of the belt and the point, and a second surface between the other end of the rear surface of the belt and the point,
    wherein the first pad overlaps the central point of the belt to contact a lumbar region, and the second pad overlaps the lateral surface of the belt to contact an oblique abdominal region, thereby enabling simultaneous stimulation of lumbar and abdominal muscles.

\* \* \* \* \*